(12) United States Patent
Garrity (10) Patent No.: US 10,898,171 B2
(45) Date of Patent: Jan. 26, 2021

(54) BIOPSY NEEDLE FOR ACCESSING PERIPHERAL LUNG NODULES

(71) Applicant: BOSTON SCIENTIFIC SCIMED, INC., Maple Grove, MN (US)

(72) Inventor: Douglas W. Garrity, Waltham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 350 days.

(21) Appl. No.: 15/917,114

(22) Filed: Mar. 9, 2018

(65) Prior Publication Data

US 2018/0263607 A1 Sep. 20, 2018

Related U.S. Application Data

(60) Provisional application No. 62/472,128, filed on Mar. 16, 2017.

(51) Int. Cl.
*A61B 5/00* (2006.01)
*A61B 10/02* (2006.01)
*A61B 10/04* (2006.01)

(52) U.S. Cl.
CPC ...... *A61B 10/0283* (2013.01); *A61B 10/0275* (2013.01); *A61B 10/04* (2013.01); *A61B 2010/045* (2013.01)

(58) Field of Classification Search
CPC . A61B 10/02; A61B 10/0233; A61B 10/0275; A61B 10/0283; A61B 10/04
See application file for complete search history.

(56) References Cited

U.S. PATENT DOCUMENTS

| | | | | |
|---|---|---|---|---|
| 4,976,690 A | * | 12/1990 | Solar | A61M 25/0054 604/103.06 |
| 5,238,004 A | | 8/1993 | Sahatjian et al. | |
| 5,533,985 A | * | 7/1996 | Wang | A61M 25/0009 604/264 |
| 5,964,740 A | | 10/1999 | Ouchi | |

(Continued)

FOREIGN PATENT DOCUMENTS

| WO | 2014060116 A1 | 4/2014 |
|---|---|---|
| WO | 2017210333 A1 | 12/2017 |

OTHER PUBLICATIONS

Invitation to Pay Additional Fees dated May 25, 2018 for International Application No. PCT/US2018/021792 (11 pgs).

*Primary Examiner* — Max F Hindenburg
(74) *Attorney, Agent, or Firm* — Kacvinsky Daisak Bluni PLLC (57) ABSTRACT

Medical devices and methods for making and using medical devices are disclosed. An example medical device may include a pulmonary biopsy needle having a proximal end, a distal end, and an elongated body extending between the proximal end and the distal end. The needle may be configured to access a periphery of a patient's lungs and the elongated portion may have a first portion, a second portion, and a piercing tip. The first portion may have a first flexibility and the second portion may have a second flexibility that is more flexible than the first flexibility. The second portion may extend distally of the first portion and the second flexibility may be constant along a length of the second portion. The first portion of the needle may have a wall-thickness different than a wall-thickness of the second portion of the needle.

20 Claims, 7 Drawing Sheets

(56) References Cited

U.S. PATENT DOCUMENTS

| | | |
|---|---|---|
| 6,086,543 A | 7/2000 | Anderson et al. |
| 6,508,803 B1 | 1/2003 | Horikawa et al. |
| 2006/0100687 A1 | 5/2006 | Fahey et al. |
| 2006/0189891 A1 | 8/2006 | Waxman et al. |
| 2012/0289911 A1 | 11/2012 | Chin et al. |
| 2013/0225997 A1 | 8/2013 | Dillard et al. |
| 2014/0276051 A1 | 9/2014 | Hoffman et al. |
| 2015/0141868 A1 | 5/2015 | Clark et al. |
| 2016/0178519 A1 | 6/2016 | Zupkofska et al. |
| 2016/0287223 A1 | 10/2016 | Hingston et al. |
| 2016/0361047 A1 | 12/2016 | Rohl et al. |
| 2016/0361088 A1 | 12/2016 | Maguire et al. |

\* cited by examiner

BIOPSY NEEDLE FOR ACCESSING PERIPHERAL LUNG NODULES

CROSS REFERENCE TO RELATED APPLICATIONS

The present application claims the benefit of and priority to U.S. Provisional Patent Application Ser. No. 62/472,128, filed Mar. 16, 2017, the disclosure of which is incorporated herein by reference.

TECHNICAL FIELD

The present disclosure pertains to medical devices, and methods for manufacturing and/or using medical devices. More particularly, the present disclosure pertains to biopsy needles.

BACKGROUND

A wide variety of medical devices have been developed for medical use, for example, pulmonary use. Some of these devices include catheters, stents, diagnostic tools, and the like, and delivery devices and/or systems used for delivering such devices. These devices are manufactured by any one of a variety of different manufacturing methods and may be used according to any one of a variety of methods. Of the known medical devices, delivery system, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides, design, material, manufacturing method, and use alternatives for medical devices. In a first aspect, a pulmonary biopsy needle may comprise a proximal end, a distal end, an elongated body extending between the proximal end and the distal end, where the elongated body may have a first portion, a second portion, and a piercing tip, the first portion may have a first level of flexibility and the second portion may have a second level of flexibility that is more flexible than the first level of flexibility, the second portion may have a length extending between a first end and a second end of the second portion, and the second level of flexibility of the second portion may be constant along the length of the second portion, and the second portion of the elongated body may be distal of a distal end of the first portion of the elongated body.

In addition or alternative, and in a second aspect, the first level of flexibility may be between 3.0 lbf/in and 4.0 lbf/in and the second level of flexibility may be between 0.1 lbf/in and 1.0 lbf/in.

In addition or alternative, and in a third aspect, the elongated body may have a transition portion extending between the distal end of the first portion and a proximal end of the second portion, and the transition portion may have a level of flexibility that gradually transitions along its length from the first level of flexibility to the second level of flexibility.

In addition or alternative, and in a fourth aspect, the elongated body may comprises a lumen extending from the proximal end to a start of the piercing tip and the lumen may have a constant diameter.

In addition or alternative, and in a fifth aspect, the first portion of the elongated body may have a first outer diameter that is constant along a length extending from a proximal end of the first portion to the distal end of the first portion and the second portion of the elongated body may have a second outer diameter that is constant along a length extending from a proximal end of the second portion to a distal end of the second portion, and the second outer diameter may be less than the first outer diameter.

In addition or alternative, and in a sixth aspect, the first portion may have a central longitudinal axis that is coaxial with a central longitudinal axis of the second portion.

In addition or alternative, and in a seventh aspect, the first portion may have a first wall-thickness that is constant along a first length extending from a first end of the first portion to a second end of the first portion and the second portion may have a second wall-thickness that is less than the first wall-thickness and is constant along a second length extending from a first end of the second portion to a second end of the second portion.

In addition or alternative, and in an eighth aspect, the elongated body may have a transition portion extending between the distal end of the first portion and a proximal end of the second portion, and the transition portion may have a wall-thickness that gradually transition along its length from the first wall-thickness to the second wall-thickness.

In addition or alternative, and in a ninth aspect, a length of the second portion of the elongated body extending from a proximal end of the second portion to a distal end of the second portion may be between five inches and ten inches.

In addition or alternative, and in a tenth aspect, the elongated body may comprise a transition portion having a length extending between the distal end of the first portion and a proximal end of the second portion, and the length of the transition portion may be between 0.1 inches and 1.0 inch.

In addition or alternative, and in an eleventh aspect, a method of manufacturing a pulmonary biopsy needle may comprise selecting an elongated tube having a first wall-thickness that extends a length from a first end of the elongated tube to a second end of the elongated tube, and adjusting a wall-thickness of a distal portion of the elongated tube to a second wall-thickness that is less than the first wall-thickness, the distal portion of the elongated tube extends distally of a proximal portion of the elongated tube having the first wall-thickness.

In addition or alternative, and in a twelfth aspect, the method may further comprise adjusting a wall-thickness of a transition portion such that the wall-thickness of the transition portion gradually decreases over a length of the transition portion from the first wall-thickness to the second wall-thickness.

In addition or alternative, and in a thirteenth aspect, the adjusting a wall-thickness of a distal portion of the elongated tube may include removing material from the distal portion to reduce an outer diameter of the distal portion from a first outer diameter of the proximal portion to a second outer diameter.

In addition or alternative, and in a fourteenth aspect, removing material from the distal portion may include grinding the distal portion.

In addition or alternative, and in a fifteenth aspect, the distal portion may have a constant wall thickness.

In addition or alternative, and in a sixteenth aspect, a lumen of the elongated tube may have a constant diameter.

In addition or alternative, and in a seventeenth aspect, the distal portion of the elongated tube may have a constant flexibility level along a length of the distal portion extending from a first end of the distal portion to a second end of the distal portion.

In addition or alternative, and in an eighteenth aspect, a method for obtaining a tissue sample from a lung of a patient may comprise identifying a path in an airway that leads to a tissue sample site, introducing a flexible needle into the airway along the path, where the flexible needle may comprise a first portion with a first length having a first wall-thickness, a second portion with a second length having a second wall-thickness that is less than the first wall-thickness, and a piercing tip having a proximal end at a distal end of the second portion, navigating the flexible needle through the path to direct the piercing tip of the flexible needle to the tissue sample site, and obtaining a tissue sample from the tissue sample site.

In addition or alternative, and in a nineteenth aspect, the method may further comprise inserting the flexible needle into a lumen of a catheter.

In addition or alternative, and in a twentieth aspect, the flexible needle may have a constant inner diameter.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

The global lung cancer epidemic, combined with the adoption of lung cancer screening, may result in an increasing number of suspicious solitary pulmonary nodules (SPNs) found on chest computed tomography (CT) scans or other scans. Suspicious SPNs, which typically exist in the periphery of the lungs, may be difficult to access and diagnose using current bronchoscopic technologies designed primarily for the central airway. Peripheral lung nodules, or SPNs, may be rounded masses measuring up to 3 centimeters (cm), which can be benign or malignant. When an SPN is identified, it may need to be diagnosed with a biopsy. Typically, Fine Needle Aspiration (FNA) may be utilized to access and obtain a biopsy from identified SPNs with a transbronchial approach through a patient's throat or mouth or with a transthoracic approach through a patient's thoracic cavity. Generally, the transbronchial approach may be favored over the transthoracic approach as access to the SPNs may be gained through existing airways of the lung without puncturing body tissue. However, as SPNs are often located in the deep periphery of the lungs, it may be difficult or impossible to reach an SPN through airways of the lungs and a transthoracic approach accessing an SPN by puncturing through a patient's thoracic cavity may need to be used. As a transthoracic approach may be viewed as more invasive than a transbronchial approach that may require more recovery time than a transbronchial approach, it may be desirable to provide a device that is configured to navigate the tortuous pathways of the deep or far periphery of the lung's airways. Such a device may allow a physician to obtain biopsy samples from SPNs located in the deep or far periphery of a patient's lungs via a transbronchial approach that were not previously accessible with a transbronchial approach. While the present disclosure is described with respect to lung nodules, it is contemplated that the methods and devices described herein can be applied to other parts of the anatomy, such as, but not limited to, gastrointestinal, urological, gynecological, etc.

Figure 1:
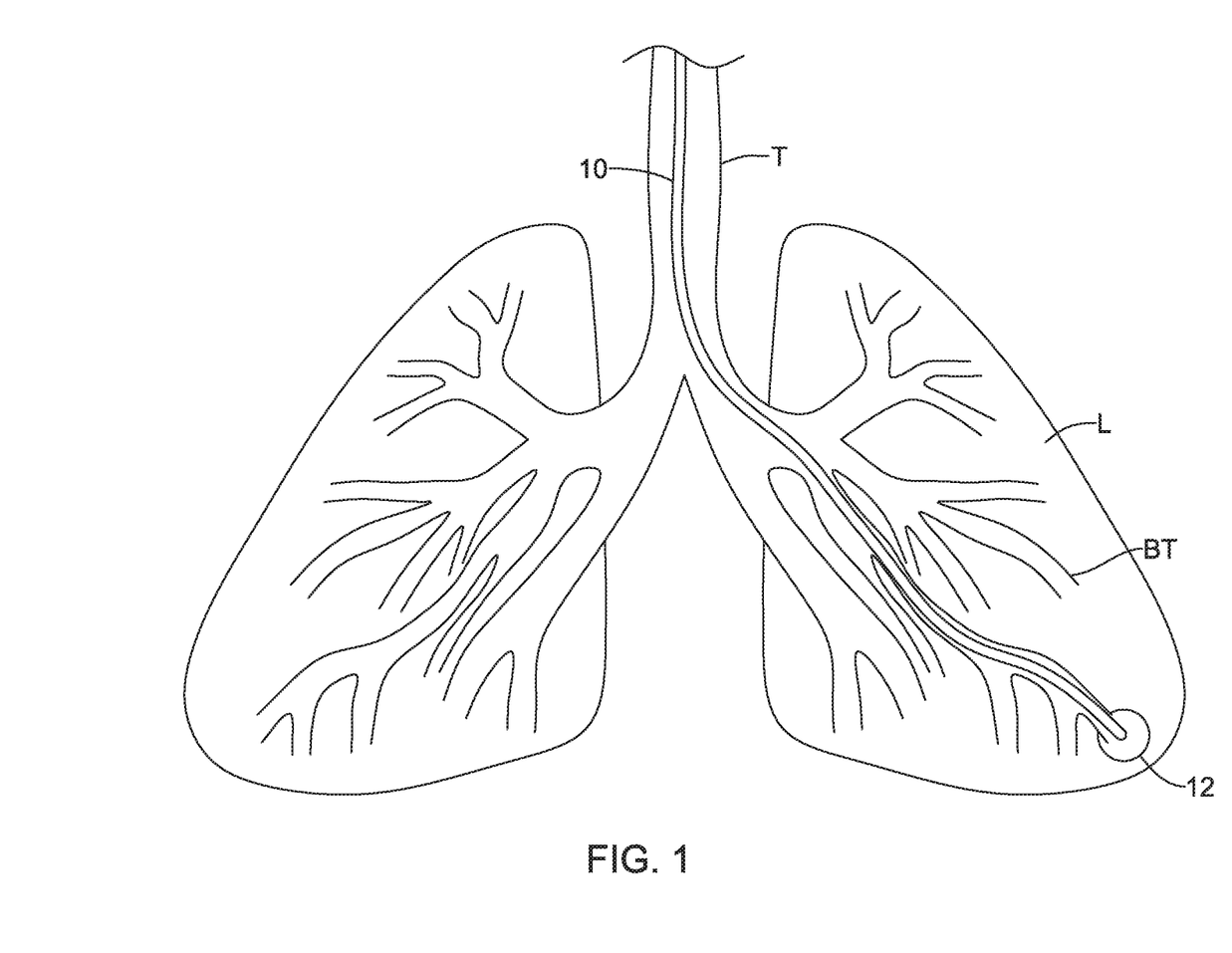
FIG. 1 is a plan view of an example biopsy tool accessing a peripheral lung nodule.

FIG. 1 illustrates a plan view of an example biopsy system 10 advanced through the trachea T and the bronchial tree BT to a peripheral nodule 12 within the lung L. In some instances, the nodule or lesion 12 may be located in the deep peripheral region of the lung which may be difficult to access due to a tortuous pathway of the airways of the peripheral region of the lungs.

Although FIG. 1 depicts the biopsy system 10 reaching the peripheral nodule 12, typical biopsy systems used with a bronchoscope in a transbronchial approach are unable to access SPNs located in the deep periphery of the lungs due to the tortuous nature of the airways at the deep periphery of the lungs. Although various gauge needles may be use in biopsy systems, including but not limited to needles having a gauge between seventeen (17) gauge and twenty-seven (27) gauge, it has been found that twenty-five (25) gauge needles may be the preferred size for attempting to access SPNs in the periphery of the lungs. As twenty-five (25) gauge needles may have an inner diameter of about 0.0120 inches and an outer diameter of about 0.0203 inches, twenty-five gauge (25) needles may provide a preferred balance between stiffness and flexibility needed to traverse airways in the lungs, while providing an inner diameter size that facilitates obtaining adequate samples once an SPN is reached with the needle. Even so, it has been found that a distal end of twenty-five (25) gauge needles may be too stiff to navigate airways of the deep periphery portions of the lungs. Further, although twenty-seven (27) gauge needles may have a more flexible distal end than twenty-five (25) gauge needles, twenty-seven (27) gauge needles may not have the proximal stiffness needed to traverse airways of the deep periphery of the lungs and/or may not have an inner diameter adequately sized (e.g., the inner diameters may be too small) to reliably obtain samples from SPNs (e.g., to reliably obtain enough of a sample from an SPN to perform required testing on the sample), if the SPNs are reached. The disclosed needles address this need by providing needles that have a proximal stiffness suitable for traversing the needles through the deep periphery of the lungs, suitable distal flexibility for navigating the deep periphery of the lungs, and suitable inner diameters (e.g., the inner diameters are large enough) for reliably obtaining adequate samples from SPNs (e.g., for reliably obtaining enough of a sample from an SPN to perform required testing on the sample) once the SPNs are located with the needles.

Figure 2:
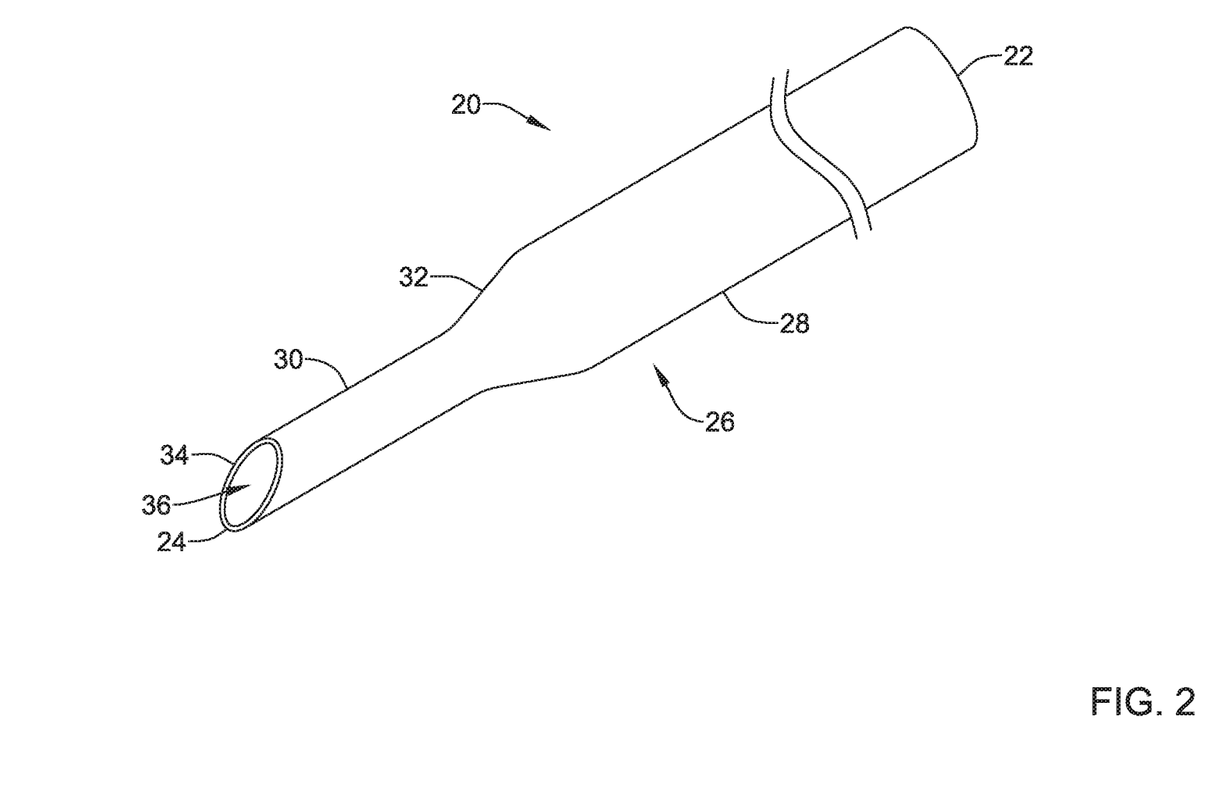
FIG. 2 is a perspective view illustrating an example biopsy needle.

FIG. 2 depicts a perspective view of a needle 20 configured to traverse the tortuous pathways of the airways in the deep periphery of a patient's lungs, while maintaining axial strength to permit the needle 20 to be inserted to a target location. The needle 20 may have a proximal end 22 and a distal end 24, with an elongated body 26 extending between the proximal end 22 and the distal end 24. To facilitate navigating to the periphery of a patient's lungs, the needle 20 or the elongated body 26 of the needle 20 may have one or more different flexibilities along its length.

The elongated body 26 may have one or more portions. In instances when the elongated body may have more than one portion, the elongated body 26 may have at least a first portion 28 and a second portion 30. Further, although not necessarily required, the elongated body may have a transition portion 32 and/or a tip portion 34 (e.g., a penetrating tip, a piercing tip, an angled tip, or other tip).

Figure 3:
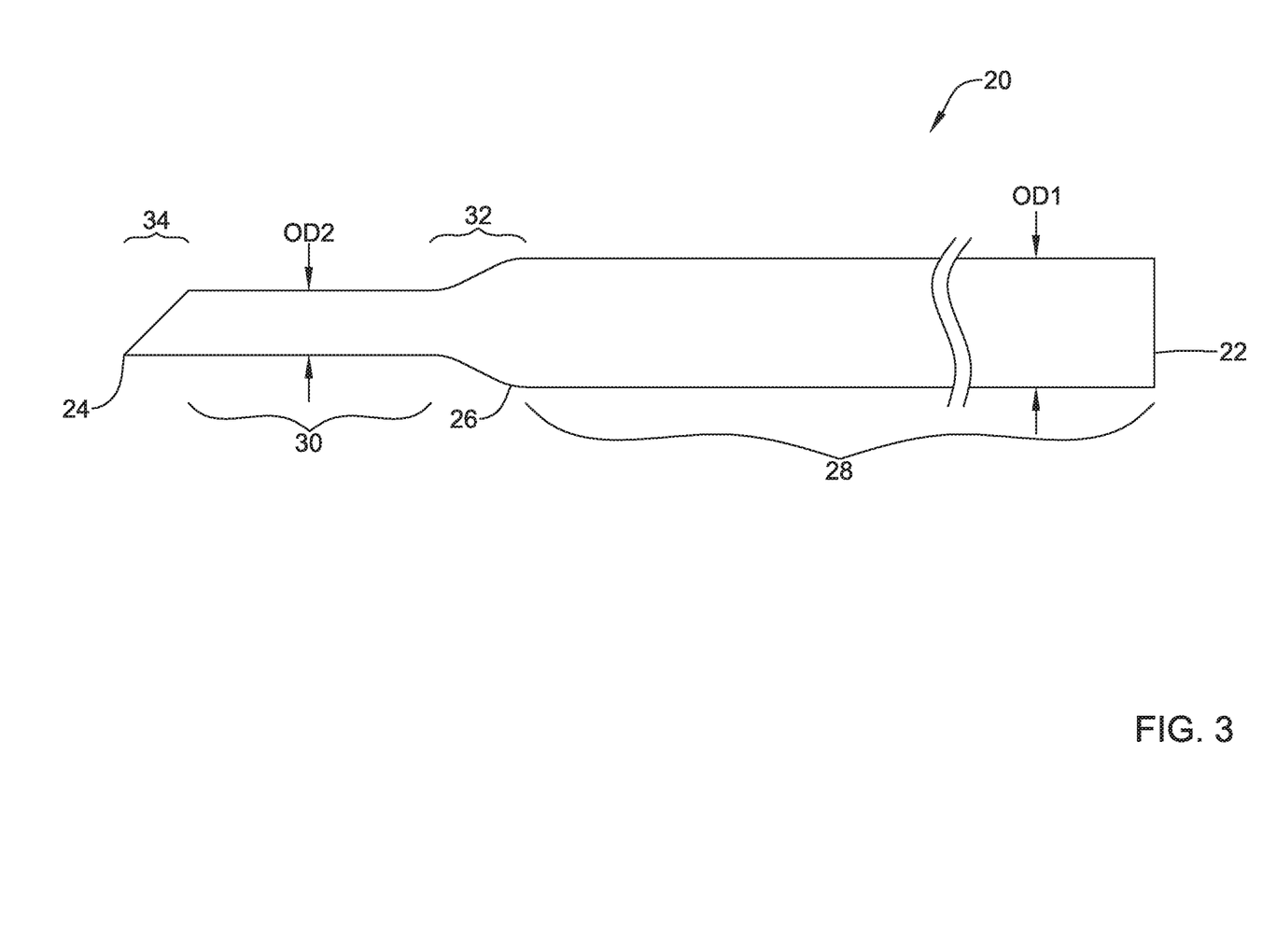
FIG. 3 is a side elevation view illustrating the example biopsy needle of FIG. 2.

FIG. 3 is a side elevation view of the needle 20. As is shown in FIG. 3, the second portion 30 of the elongated body 26 may extend distally of the first portion 28 of the elongated body 26, and in some cases, the second portion 30 (e.g., a distal portion) may be entirely distal of the first portion 28 (e.g., a proximal portion), but this is not required in all cases. In one example, the first portion 28 of the elongated body 26 may extend from the proximal end 22 of the needle 20 to a proximal end of the second portion 30. When the elongated body 26 includes the transition portion 32, as in the needle 20 of FIG. 3, the first portion 28 of the elongated body 26 may extend from the proximal end 22 of the needle 20 to a proximal end of the transition portion 32 and the transition portion 32 may extend from a distal end of the first portion 28 to a proximal end of the second portion 30. The second portion 30 may extend distally from a distal end of the transition portion 32. When the elongated body 26 includes a tip portion 34, the second portion 30 may extend from the distal end of the transition portion to a proximal end of the tip portion 34, and the tip portion 34 may extend from a distal end of the second portion 30 to the distal end 24 of the needle 20.

Each portion of the elongated body 26 may have a same or different length than another portion of the elongated body. A length of the elongated body 26 extending between the proximal end 22 (e.g., a first end) of the needle 20 and the distal end 24 (e.g., a second end) of the needle 20 may be any length depending on the application of the needle 20. For example, the elongated body 26 may have a length between about forty (40) inches and one hundred (100) inches, fifty (50) inches and ninety (90) inches, sixty (60) inches and eighty (80) inches, sixty-five (65) inches and seventy (70) inches, and/or a different length less than forty (40) inches or greater than one hundred (100) inches. A length of the first portion 28 of the elongated body 26 extending between the proximal end and the distal end of the first portion 28 may be any length depending on the application of the needle 20. For example, the first portion 28 of the elongated body 26 may have a length between about thirty (30) inches and ninety (90) inches, forty (40) inches and eighty (80) inches, fifty (50) inches and seventy (70) inches, fifty-five (55) inches and sixty (60) inches, and/or a different length less than thirty (30) inches or greater than ninety (90) inches. A length of the second portion 30 of the elongated body extending between the proximal end and the distal end of the second portion 30 may be any length depending on the application of the needle 20. For example, the second portion 30 of elongated body 26 may have a length between about two (2) inches and twenty (20) inches, four (4) inches and sixteen (16) inches, six (6) inches and twelve (12) inches, seven (7) inches and ten (10) inches, and/or a different length less than two (2) inches or greater than twenty (20) inches. Although lengths of the transition portion 32 and the tip portion 34 may vary, the transition portion 32 have a length between about 0.1 inches and two (2) inches, while the tip portion 34 may have a length less than about one inch and in some cases, typically less than half an inch.

In some instances, as disclosed here, the needle 20 may be configured to travel through airways in the deep or far periphery of a patient's lungs to reach nodules on or in the lungs. In such cases, the needle 20 may have an overall length between fifty (50) inches and eighty (80) inches (e.g., at or about sixty-six (66) inches or any other length), the first portion 28 of the needle 20 may have a length between fifty (50) inches and sixty (60) inches (e.g., at or about 56 inches or any other length), the second portion 30 may have a length between eight (8) inches and twelve (12) inches (e.g., at or about 9.5 inches or any other length), the transition portion 32 may be between about 0.4 inches and 0.6 inches (e.g., at or about 0.5 inches or any other length), and the tip portion 34 may have a length that is less than about 0.5 inches.

Although FIG. 3 depicts one example of a configuration of the needle 20 including the first portion 28, the second portion 30, the transition portion 32, and the tip portion 34, one or more of these portions may be removed from the needle 20 and/or one or more portions may be added to the needle 20. For example, in some cases, the needle 20 may not include the transition portion 32. Alternatively, or in addition, the needle 20 may include one or more additional elongated portions (e.g., similar to one or both of the first portion 28 and the second portion 30) and/or one or more additional transition portions. In one example of an elongated body including one or more additional elongated portions, the first portion 28 and the second portion 30 may be the two distal-most elongated portions and/or the second portion 30 may be the distal-most elongated portion. In some cases, additional elongated portions and/or transition portions may facilitate adding one or more portions of the elongated body 26 having a flexibility (e.g., a level of flexibility) different than another portion of the elongated body 26, where the additional portions may be utilized to increase or decrease flexibility/stiffness in the needle 20 at localized areas to facilitate accessing particular anatomy of a patient and/or facilitate use with an ancillary medical device (e.g., a scope or other medical device).

As shown in FIG. 3, the first portion 28 of the elongated body 26 may have a first outer diameter OD1 and the second portion 30 of the elongated body 26 may have a second outer diameter OD2. The second outer diameter OD2 may be smaller than the first outer diameter OD1. In one example, the second outer diameter OD2 may be smaller than the first outer diameter OD1 by between about 0.001 inches and 0.007, by between about 0.002 and 0.006 inches, by between about 0.003 inches and 0.005 inches, by about 0.004 inches, or by a larger or smaller amount. Further, in some cases, the first outer diameter OD1 of the first portion 28 of the elongated body 26 may be constant along a length extending from the proximal end of the first portion 28 to the distal end of the first portion 28, but this is not required. Similarly, in some cases, the second outer diameter OD2 of the second portion 30 of the elongated body 26 may be constant along a length extending from the proximal end of the second portion 30 to the distal end of the second portion 30, but this is not required. The relative outer diameters of the first portion 28 and the second portion 30 may facilitate providing the second portion 30 with a flexibility that is different than a flexibility of the first portion 28.

The transition portion 32, when included in the needle 20, may have an outer diameter that tapers from about the first outer diameter OD1 of the first portion 28 to about the second outer diameter OD2 of the second portion 30. In some cases, the taper of the outer diameter of the transition portion 32 may have a constant slope. Alternatively, the outer diameter of the transition portion 32 may have two or more different slopes, the transition portion 32 may have an outer diameter that is reduced from the first outer diameter OD1 to the second outer diameter OD2 in a step-wise manner, and/or the outer diameter of the transition portion 32 may transition from the first outer diameter OD1 to the second outer diameter OD2 in any other manner.

Figure 4:
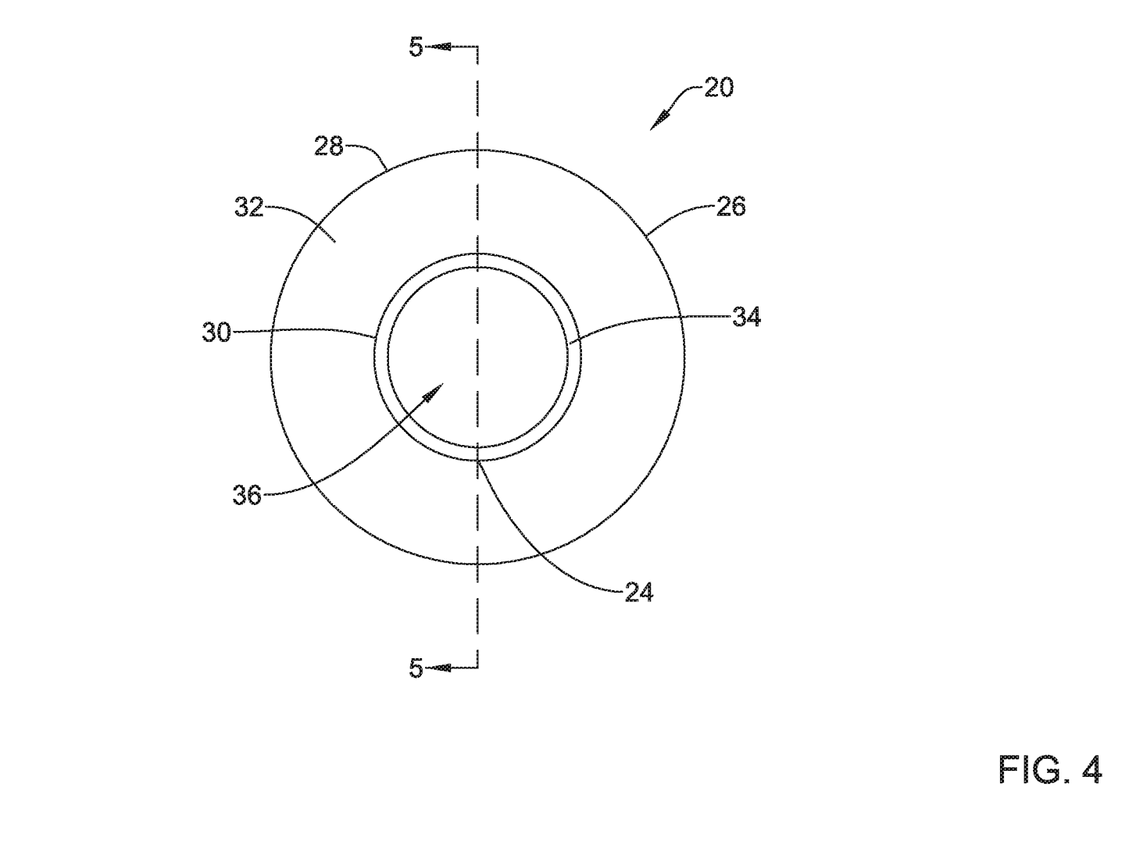
FIG. 4 is an end elevation view illustrating the example biopsy needle of FIG. 2.

FIG. 4 is a distal end elevation view of the needle 20 depicted in FIGS. 2 and 3. The needle 20 depicts the elongated body 26 of the need 20 with the transition portion 32 extending from the first portion 28 to the second portion 30 and the second portion 30 extending to the tip portion 34, which may be the distal-most portion of the elongated body 26. Further, the elongated body 26 may define a lumen 36 having a diameter defined by the inner diameter(s) of the elongated body 26.

Figure 5:
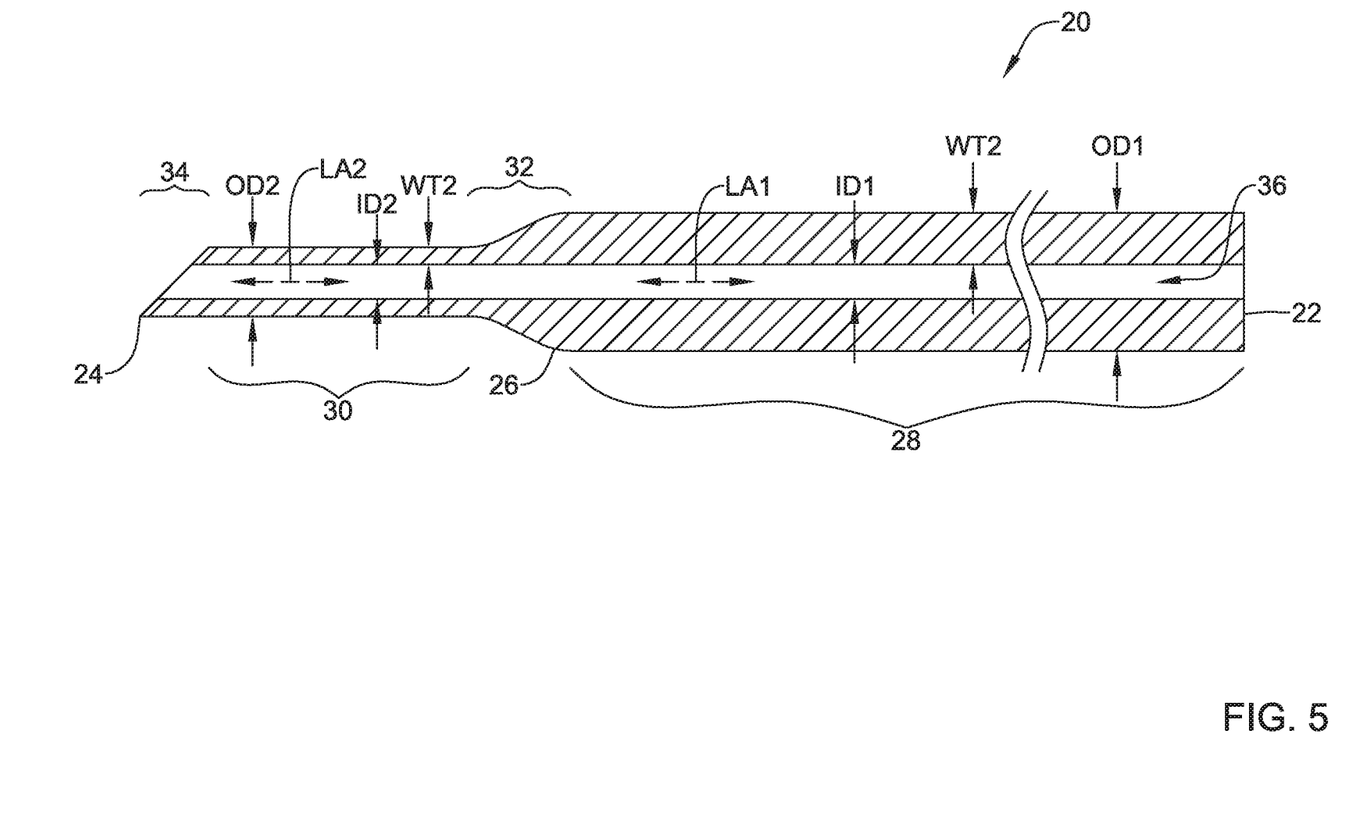
FIG. 5 is a cross-sectional view illustrating the example biopsy needle of FIG. 2, take along line 5-5 in FIG. 4.

FIG. 5 is a cross-sectional view of the needle 20 taken along line 5-5 in FIG. 4. The first portion 28 of the elongated body 26 may have a first inner diameter ID1 and the second portion 30 of the elongated body 26 may have a second inner diameter ID2. The second inner diameter ID2 may be equal to first inner diameter ID1. Further, in some cases, the first inner diameter ID1 of the first portion 28 of the elongated body 26 may be constant along the length extending from the proximal end of the first portion 28 to the distal end of the first portion 28, but this is not required. Similarly, in some cases, the second inner diameter ID2 of the second portion 30 of the elongated body 26 may be constant along the length extending from the proximal end of the second portion 30 to the distal end of the second portion 30, but this is not required. When present, the transition portion 32 may have an inner diameter that may be constant along the length extending from the proximal end of the transition portion 32 to the distal end of the transition portion 32. In some cases, the inner diameters of the first portion 28, the second portion 30, and the transition portion 32 may, along with any other portion extending between the proximal end 22 of the needle 20 and the proximal end of the tip portion 34, may be the same inner diameter such that the elongated body 26 may have a constant inner diameter extending from a proximal end 22 of the needle to the proximal end of the tip portion 34. However, it is contemplated that one or more portions of the elongated body 26 may have an inner diameter that varies along that portion and/or is different than one or more other portions of the elongated body 26.

FIG. 5 depicts the lumen 36 extending from the proximal end 22 of the needle 20 to the distal end of the second portion 30 and out the tip portion 34. The lumen 36 may have a constant diameter along the length of the needle as defined by the inner diameter of the elongate body 26. In some cases, the lumen 36 may have a central longitudinal axis along a first longitudinal axis LA1 of the first portion 28 and a second longitudinal axis LA2 of the second portion 30. In one example, the first longitudinal axis LA1 may be co-axial with the second longitudinal axis LA2, but this is not required. A wall-thickness of the elongated body 26 may be determined by subtracting an inner diameter of the elongated body 26 from an outer diameter of the elongated body 26. In some cases, as may be the case when the elongated body 26 or at least the first portion 28 and the second portion 30 of the elongated body 26 are formed from a same material, the wall-thickness of the elongated body 26, along with the material properties of the material of the elongated body, may determine the flexibility of the elongated body 26 and/or the flexibility of each portion of the elongated body 26 (e.g., the first portion 28, the second portion 30, the transition portion 32, the tip portion 34, and/or other portions of the elongated body 26).

As shown in FIG. 5, the first portion 28 of the elongated body 26 may have a first wall-thickness WT1, which is equal to the first outer diameter OD1 minus the first inner diameter ID1. The second portion 30 of the elongated body 26 may have a second wall-thickness WT2, which is equal to the second outer diameter OD2 minus the second inner diameter ID2. When the transition portion 32 is included in the elongated body 26, the transition portion 32 may have a wall-thickness that transitions from the first wall-thickness WT1 to the second wall-thickness WT2 in a manner similar to how the outer diameter of the transition portion 32 transitions from the first outer diameter OD1 to the second outer diameter OD2. Additional elongated portions, when included in the elongated body 26, may have similar of different wall-thickness to the first wall-thickness WT1 and/or the second wall-thickness WT2, but this is not required.

In the example of FIG. 5, the first portion 28 of the elongated body 26 may have a constant wall-thickness WT1 giving the first portion 28 a constant flexibility. However, the first portion 28 of the elongate body 26 may have a wall-thickness that varies along its length and thus, a flexibility that varies along its depending on a desired proximal stiffness or flexibility. In the example of FIG. 5, the second portion 30 of the elongated body 26 may have a constant wall-thickness WT2 giving the second portion a constant flexibility. However, the second portion 30 of the elongated body 26 may have a wall-thickness that varies along its length and thus, a flexibility that varies along its length depending on a desired distal stiffness or flexibility.

In one example of a needle 20 configured to reach SPNs in the deep periphery of the lungs and traverse the airways of the lungs to reach the SPNs, the elongated body may have a first portion 28 that has a first wall-thickness WT1 between about 0.0069 inches and 0.0091 inches (e.g., a wall-thickness of a twenty-five (25) gauge needle), a second portion 30 that has a second wall-thickness WT2 between about 0.0029 inches and 0.0051 inches, and a constant inner diameter of between about 0.0119 inches and 0.0121 inches (e.g., an inner diameter of a twenty-five (25) gauge needle). Such a configured needle 20 may provide a proximal stiffness or flexibility required to traverse airways of the deep periphery of the lungs with the needle 20 and a distal stiffness or flexibility required to traverse the tortuous path of the deep periphery of the lungs, while maintaining an inner diameter (e.g., a size of the lumen 36) sized to reliably obtain adequate samples of the SPNs or nodules located in the deep periphery of the lungs (e.g., the distal stiffness or flexibility of the needle 20 is reduced without sacrificing the size of the lumen 36 and thus, the same amount of sample from an SPN can be obtained as otherwise would have been available without reducing an outer diameter or wall thickness of the second portion 30 of the needle 20).

Further, the first portion 28 and the second portion 30 of a needle 20 having the size configurations discussed in the previous paragraph may be monolithically formed from a single piece of material. When such a needle 20 is configured of cobalt chromium, the first portion 28 of the needle 20 may have a flexibility of about 3.6 lbf/in and the second portion 30 of the needle 20 may have a flexibility of about 0.9 lbf/in (e.g., a 75% increase in flexibility over the flexibility of the first portion 28), where the flexibility of each portion 28, 30 of the needle 20 may be measured by a three-point bend test common in the industry for measuring flexibility. When the first portion 28 and the second portion 30 of the needle 20 are monolithically formed (e.g., monolithically formed from a biocompatible stainless steel (e.g., cobalt chromium or other stainless steel)), the needle 20 may have advantages over typical needles used for traversing airways of the lungs (e.g., needles having a distal portions of standard 25-gauge cobalt chromium, of standard 25-gauge 300 series stainless steel, of 25-gauge cobalt chromium with a spiral cut (e.g., 0.120 inch pitch-0.200 inch pitch), of standard 25-gauge nitinol) that include, but are not limited to, maintaining proximal stiffness and a quantity of sample that may be obtained from a needle, while increasing distal flexibility and reducing material and manufacturing costs.

Figure 6:
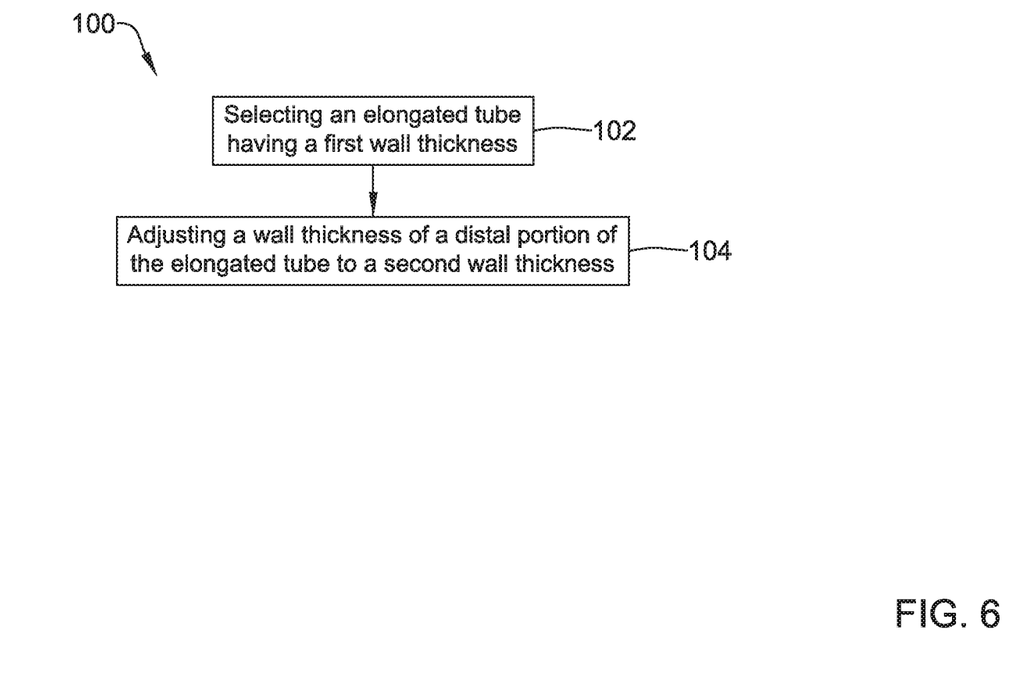
FIG. 6 is a flow diagram illustrating an example method of manufacturing a biopsy needle.

The needle 20 disclosed herein may be made by one or more manufacturing techniques. Method 100, depicted in FIG. 6, provides an example method for manufacturing the needle 20. The method 100 may include selecting 102 an elongated tube. The selected elongated tube may have a first wall-thickness (e.g., the first wall-thickness WT1 discussed above or a different first wall-thickness) and/or a specified gauge (e.g., twenty-five (25) gauge or other gauge). In some cases, the selected elongated tube may have a first wall thickness of between about 0.0069 inches and 0.0091 inches (e.g., with a first outer diameter between about 0.0190 inches and 0.0210 inches with an inner diameter between about 0.0119 inches and 0.0121 inches).

The selected elongated tube may be a pre-formed needle having a tip portion (e.g., a piercing tip, penetrating tip, sharpened or other tip portion). Alternatively, the selected elongated tube may be a raw tube and a tip portion may be added to a distal end of the selected needle.

The selected elongated tube may be formed of any desirable material. In one example, the selected elongated tube may be formed entirely from or at least partially from a biocompatible stainless steel (e.g., cobalt chromium or other biocompatible stainless steel). In some cases, the elongated tube may be a monolithic tube or may be formed from two or more materials integrally connected.

Once the elongated tube has been selected, a wall thickness of a distal portion of the elongated tube may be adjusted 104 to a second wall thickness (e.g., the second wall-thickness WT2 discussed above or a different second wall-thickness) that is less than the first wall thickness. The adjusted second wall-thickness may be any size. In some cases, the adjusted wall thickness may be between about 0.0029 inches and 0.0051 inches (e.g., with a second outer diameter between about 0.0150 inches and 0.0170 inches and an inner diameter between about 0.0119 inches and 0.0121 inches). When such an elongated tube is formed and the elongated tube is formed from cobalt chromium, the flexibility or stiffness of the proximal portion may be about 3.6 lbf/in and the flexibility or stiffness of the distal portion may be about 0.9 lbf/in, as measured by the standard 3-point bend test.

The distal portion of the selected elongated tube may be a portion of the elongated tube that extends distally of a proximal portion of the elongated tube. In some cases, the distal portion of the selected elongated tube may extend proximally from a distal end of the elongated tube or from a proximal end of a tip portion of the elongated tube a distance between about eight (8) inches and about twelve (12) inches. In one example, the distal portion of the selected elongated tube may be the second portion 30 of the elongated body 26 discussed above.

In some cases, the second wall-thickness of the distal portion of the elongated tube may be constant along the length of the distal portion. Such a constant wall-thickness may result in the distal portion having a constant flexibility along the length of the distal portion to facilitate traversing a tortuous path of the deep periphery of the lungs.

In some cases, the method 100 may include adjusting a wall thickness of a transition portion of the selected elongated tube (e.g., the transition portion 32 of the elongated body 26 discussed above or a different transition portion). Adding a transition portion to the selected elongated tub may increase a stability of tube and mitigate a likelihood of the distal portion with the adjusted second wall-thickness breaking away from the proximal portion having the first wall-thickness when compared to such an elongated tube without the transition portion (e.g., an elongated tube with a shoulder between the proximal portion with the first wall-thickness and the distal portion with the second wall thickness).

When creating a transition portion in the selected elongated tube, the transition portion may have a wall-thickness that is gradually reduced from the first wall-thickness to the second wall-thickness over a length of the transition portion. In one example, the transition portion may have a wall-thickness that gradually transitions from the first wall-thickness to the second wall-thickness over a length of about 0.400 inches to about 0.600 inches. In some cases, the length of the transition portion is about one hundred (100) times greater than a difference between the first wall thickness and the second wall thickness, but this is not required.

The wall-thickness of the selected elongated tube may be adjusted in any manner. In some cases, the wall-thickness of the selected elongated tube may be adjusted by removing material from an outer diameter of the elongated tube (e.g., from the distal portion and/or the transition portion). Alternatively, or in addition, adjusting a wall thickness of a distal portion of the elongated tube relative to the proximal portion of the elongated tube may include adding material to the elongated tube (e.g., to the proximal portion and/or the transition portion) and/or otherwise manipulating relative sizes of wall-thicknesses of elongated tube portions through typical tube forming techniques including, but not limited to, extrusion, drawing, and/or other techniques.

When material is removed from the outer diameter of the elongated tube to adjust a wall-thickness of the distal portion, any removal technique may be utilized. In one example, the distal portion of the selected elongated tube may be ground to a desired outer diameter to form a wall-thickness having desired flexibility. Other removal techniques may be utilized as desired, which may include but are not limited to milling techniques, turning techniques, honing techniques, lapping techniques, planning techniques, and/or other removal techniques.

A needle created from the method 100 may take on various forms having a distal-most elongated portion having a flexibility that is less than a flexibility of a more proximal elongated portion. In one example, a needle created from the method 100 may have a tip portion (e.g., the tip portion 34 or other tip portion), a distal portion (e.g., the second portion 30 or other distal portion) extending proximally from the tip portion, and a proximal portion (e.g., the first portion 28 or other proximal portion) extending proximally of the distal portion, where the distal portion has a greater flexibility than a flexibility of the proximal portion, the distal portion and the proximal portion have an inner diameter that is constant from a proximal end of the proximal portion to a distal end of the distal portion, and the distal portion and the proximal portion are monolithically formed. In some cases, the created needle may have a transition portion (e.g., the transition portion 32 or other transition portion) between the proximal portion and the distal portion, where the transition portion has a flexibility that gradually transition from a flexibility at about the flexibility of the proximal portion to the flexibility of the distal portion, has the same inner diameter as the distal portion and the proximal portion, and is monolithically formed with the distal portion and the proximal portion. However, other configurations are contemplated, including needles configured from two or more materials and/or needles having one or more portions proximal of the proximal portion.

Figure 7:
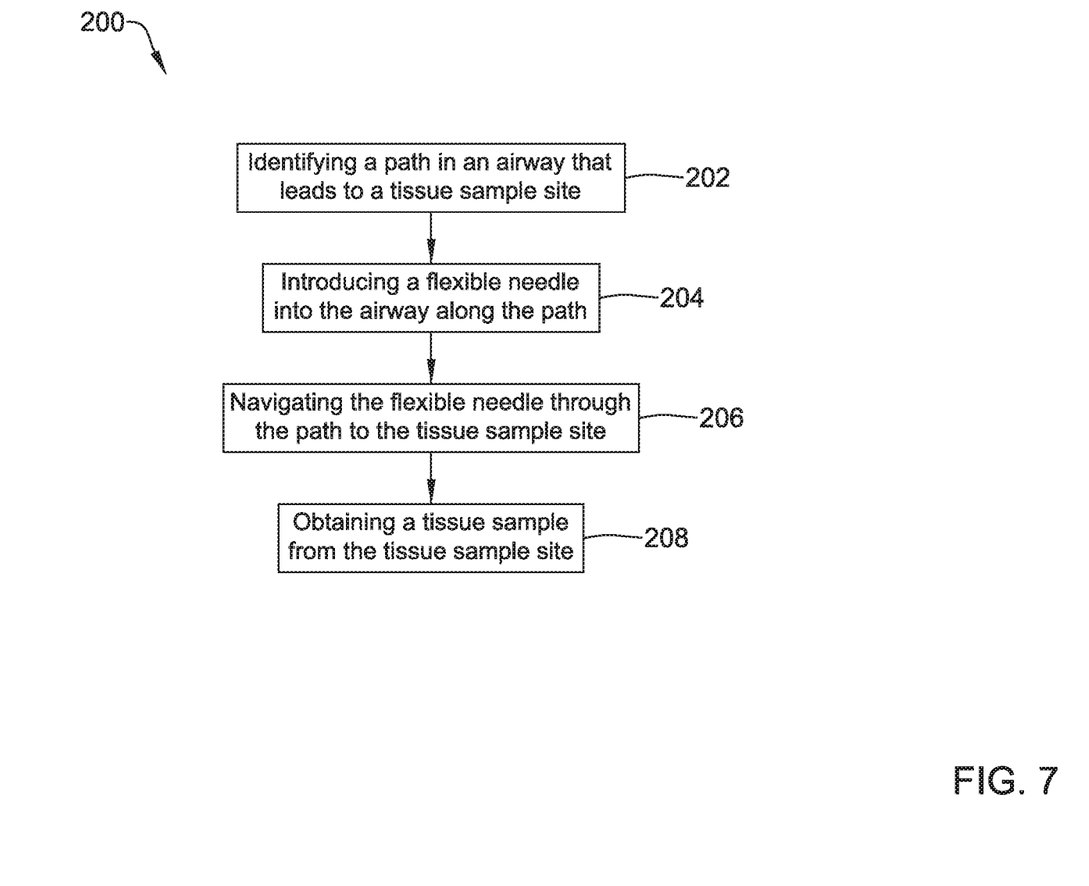
FIG. 7 is a flow diagram illustrating an example method of using a biopsy needle.

FIG. 7 depicts a method 200 of using a flexible needle (e.g., the needle 20 or other needle) in a procedure to obtain a tissue sample from a lung of a patient. The method 200 may include identifying 202 a path in an airway that leads to a tissue sample site. The path in the airway may be identified in any manner. In one example, the path may be identified in the same or different CT scan that may be used to identify an SPN or other nodule (e.g., a target site). Alternatively, one or more other scans or imaging techniques may be utilized to identify a path through the airways of the lungs to the target site. Once the path has been identified, the flexible needle (e.g., the needle 20 having a constant inner diameter or other needle) may be introduced 204 into the airway along the identified path. Introducing the flexible needle to the path may include inserting the flexible needle into a lumen of a catheter and/or a lumen of a bronchoscope. The flexible needle may include a first portion (e.g., the first portion 28 or other first portion) having a length with a first wall-thickness (e.g., the first wall-thickness WT1 discussed above or a different wall-thickness), a second portion (e.g., the second portion 30 or other second portion) having a length with a second wall-thickness (e.g., the second wall-thickness WT2 discussed above or a different wall-thickness) that is less than the first wall-thickness, and a tip portion (e.g., the tip portion 34 having a piercing tip, a penetrating tip, a sharpened tip, or other tip portion) having a proximal end at a distal end of the second portion.

After the flexible needle has been inserted into the identified path, the method 200 may include navigating 206 the flexible needle through the identified path to the target sample site (e.g., to an SPN or other nodule). Once the target sample site has been reached, the method may include obtaining 208 a tissue sample from the tissue sample site (e.g., from the SPN or other nodule). In some cases, the sample may be obtained by engaging the tip portion of the flexible needle with the SPN or nodule or other tissue and while the tip portion is engaged with the SPN or nodule or other tissue, withdrawing a syringe that is in communication with the flexible needle to pull a vacuum through the lumen of the flexible needle and draw a sample into the lumen of the needle. After obtaining the sample, the sample and/or the flexible needle may be withdrawn from the patient and the sample may be confirmed as being from the SPN or nodule. If the sample is not confirmed as being a sample from the SPN or nodule, the method 200 may be repeated.

As discussed above with respect to the needle 20, the flexible needle may have a constant inner diameter or diameter of a lumen thereof that is configured to facilitate obtaining adequate sample sizes from SPNs or other nodules, while having a distal end with an increased flexibility. In such configured flexible needles, the size of the inner diameter or diameter of the lumen of the flexible needle may allow for a greater vacuum force in the lumen of the needle to better collect a sample in response to withdrawing the syringe when compared to a vacuum force that could be obtained with a needle in which a wall-thickness of a distal end of the needle and an inner diameter of the distal end are reduced to increase flexibility in the distal end.

Although specific materials may be discussed above for the needle 20, the needle 20 may include any material commonly associated with medical devices. For simplicity purposes, the following discussion makes reference to the needle 20. However, this is not intended to limit the devices and methods described herein, as the discussion may be applied to other similar systems and/or components of systems or devices disclosed herein.

The needle 20 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the needle 20 may be doped with, made of, or otherwise include a radiopaque material. Radiopaque materials are understood to be materials capable of producing a relatively bright image on a fluoroscopy screen or another imaging technique during a medical procedure. This relatively bright image aids the user of the needle 20 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the needle 20 to achieve the same result.

In some embodiments, a degree of Magnetic Resonance Imaging (MRI) compatibility is imparted into the needle 20. For example, the needle 20, or portions or components thereof, may be made of a material that does not substantially distort the image and create substantial artifacts (i.e., gaps in the image). Certain ferromagnetic materials, for example, may not be suitable because they may create artifacts in an MRI image. The needle 20, or portions thereof, may also include and/or be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A pulmonary biopsy needle comprising:
   a proximal end;
   a distal end; and
   an elongated body monolithically formed from a shape memory material, the elongated body extending between the proximal end and the distal end; wherein:
   the elongated body has a first portion, a second portion, and a piercing tip;
   the first portion has a first level of flexibility and the second portion has a second level of flexibility that is more flexible than the first level of flexibility;
   the second portion has a length extending between a first end and a second end of the second portion, and the second level of flexibility of the second portion is constant along the length of the second portion; and
   the second portion of the elongated body is distal of a distal end of the first portion of the elongated body.

2. The pulmonary biopsy needle of claim 1, wherein the first level of flexibility is between 3.0 lbf/in and 4.0 lbf/in and the second level of flexibility is between 0.1 lbf/in and 1.0 lbf/in.

3. The pulmonary biopsy needle of claim 1, wherein the elongated body has a transition portion extending between the distal end of the first portion and a proximal end of the second portion, and the transition portion has a level of flexibility that gradually transitions along its length from the first level of flexibility to the second level of flexibility.

4. The pulmonary biopsy needle of claim 1, wherein the elongated body comprises a lumen extending from the proximal end to a start of the piercing tip and the lumen has a constant diameter.

5. The pulmonary biopsy needle of claim 1, wherein the first portion of the elongated body has a first outer diameter that is constant along a length extending from a proximal end of the first portion to the distal end of the first portion and the second portion of the elongated body has a second outer diameter that is constant along a length extending from a proximal end of the second portion to a distal end of the second portion, and the second outer diameter is less than the first outer diameter.

6. The pulmonary biopsy needle of claim 5, wherein the first portion has a central longitudinal axis that is coaxial with a central longitudinal axis of the second portion.

7. The pulmonary biopsy needle of claim 1, wherein the first portion has a first wall-thickness that is constant along a first length extending from a first end of the first portion to a second end of the first portion and the second portion has a second wall-thickness that is less than the first wall-thickness and is constant along a second length extending from a first end of the second portion to a second end of the second portion.

8. The pulmonary biopsy needle of claim 1, wherein a length of the second portion of the elongated body extending from a proximal end of the second portion to a distal end of the second portion is between five inches and ten inches.

9. The pulmonary biopsy needle of claim 1, wherein the elongated body comprises a transition portion having a length extending between the distal end of the first portion and a proximal end of the second portion, and the length of the transition portion is between 0.1 inches and 1.0 inch.

10. A method of manufacturing a pulmonary biopsy needle, the method comprising:
    monolithically forming an elongated tube from a shape memory material, the elongated tube having a first wall-thickness that extends a length from a first end of the elongated tube to a second end of the elongated tube;
    adjusting a wall-thickness of a distal portion of the elongated tube to a second wall-thickness that is less than the first wall-thickness, the distal portion of the elongated tube extends distally of a proximal portion of the elongated tube having the first wall-thickness.

11. The method of claim 10, furthering comprising:
    adjusting a wall-thickness of a transition portion such that the wall-thickness of the transition portion gradually decreases over a length of the transition portion from the first wall-thickness to the second wall-thickness.

12. The method of claim 10, wherein the adjusting a wall-thickness of a distal portion of the elongated tube includes removing material from the distal portion to reduce an outer diameter of the distal portion from a first outer diameter of the proximal portion to a second outer diameter.

13. The method of claim 10, wherein the distal portion has a constant wall thickness.

14. The method of claim 10, wherein a lumen of the elongated tube has a constant diameter.

15. The method of claim 10, wherein the distal portion of the elongated tube has a constant flexibility level along a length of the distal portion extending from a first end of the distal portion to a second end of the distal portion.

16. A method for obtaining a tissue sample from a lung of a patient, the method comprising:
    identifying a path in an airway that leads to a tissue sample site;
    introducing a flexible needle into the airway along the path, wherein the flexible needle is monolithically formed from a shape memory material and comprises a first portion with a first length having a first wall-thickness, a second portion with a second length having a second wall-thickness that is less than the first wall-thickness, and a piercing tip having a proximal end at a distal end of the second portion;
    navigating the flexible needle through the path to direct the piercing tip of the flexible needle to the tissue sample site; and
    obtaining a tissue sample from the tissue sample site.

17. The method of claim 16, further comprising:
   inserting the flexible needle into a lumen of a catheter.

18. The method of claim 16, wherein the flexible needle has a constant inner diameter.

19. The pulmonary biopsy needle of claim 1, wherein the shape memory material comprises a linear elastic or non-super-elastic material.

20. The method of claim 10, wherein the shape memory material comprises a linear elastic or non-super-elastic material.

* * * * *